(12) United States Patent
Hamlin (10) Patent No.: US 9,884,082 B2
(45) Date of Patent: *Feb. 6, 2018

(54) COMPOSITIONS AND METHODS FOR ALLEVIATING HYPOSALIVATION AND FOR PROVIDING ORAL COMFORT

(71) Applicant: David A. Hamlin, Francestown, NH (US)

(72) Inventor: David A. Hamlin, Francestown, NH (US)

(73) Assignee: David A. Hamlin, Francestown, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/422,732

(22) Filed: Feb. 2, 2017

(65) Prior Publication Data

US 2017/0151302 A1 Jun. 1, 2017

Related U.S. Application Data

(63) Continuation-in-part of application No. 14/551,507, filed on Nov. 24, 2014, now Pat. No. 9,597,278, (Continued)

(51) Int. Cl.
*A61K 36/87* (2006.01)
*A61K 36/752* (2006.01)
*A61K 9/00* (2006.01)

(52) U.S. Cl.
CPC ........... *A61K 36/87* (2013.01); *A61K 9/006* (2013.01); *A61K 36/752* (2013.01)

(58) Field of Classification Search
None
See application file for complete search history.

(56) References Cited

U.S. PATENT DOCUMENTS 4,820,506 A 4/1989 Kleinberg et al.
4,938,963 A 11/1990 Parnell
(Continued)

FOREIGN PATENT DOCUMENTS

AU 2008221548 A1 8/2010
CA 2337152 2/2000
(Continued)

OTHER PUBLICATIONS

Sano et al. "Procyanidin B1 Detected in Human Serum after Intake of Proanthocyanidin-rich Grape Seed Extract", Biosci. Biotechnol., 67(5), 1140-1143, 2003.*
(Continued)

*Primary Examiner* — Isis Ghali
(74) *Attorney, Agent, or Firm* — Joseph F. Aceto, Esq.

(57) ABSTRACT

Various compositions and methods are provided to alleviate one or more symptoms associated with hyposalivation and/or xerostomia. Preferred compositions and methods employ one or more plant pulp products and/or a proanthocyanidin at a concentration effective to reduce or eliminate the symptoms. Especially preferred product components are isolated from a fruit and/or seed (e.g., grape, cranberry, blue berry, black berry, etc.), and where a second component is preferably a freeze-dried pulp from a citrus fruit (e.g., lemon, orange, lime, grapefruit, tangerine, mandarin orange, ugli fruit, etc.) not containing peel or juice therein.

8 Claims, 3 Drawing Sheets

Delta WT Saliva of Subject Based on Xeros Test Using Resting Saliva Measures

Related U.S. Application Data which is a continuation-in-part of application No. 13/129,210, filed as application No. PCT/US2009/064453 on Nov. 13, 2009, now abandoned.

(60) Provisional application No. 61/114,329, filed on Nov. 13, 2008.

(56) References Cited

U.S. PATENT DOCUMENTS

| | | | |
|---|---|---|---|
| 4,980,177 A | 12/1990 | Subraman et al. | |
| 4,997,654 A | 3/1991 | Corsalio et al. | |
| 5,156,845 A | 10/1992 | Grodberg | |
| 5,162,128 A * | 11/1992 | Mills | A23L 33/22 426/590 |
| 5,260,282 A | 11/1993 | Attstrom et al. | |
| 5,541,185 A | 7/1996 | Turgeon | |
| 5,580,880 A | 12/1996 | Handa et al. | |
| 5,614,207 A | 3/1997 | Shah et al. | |
| 5,658,554 A | 8/1997 | Fisher et al. | |
| 6,027,715 A | 2/2000 | Pozuelo | |
| 6,054,119 A | 4/2000 | Hume et al. | |
| 6,159,459 A | 12/2000 | Hunter et al. | |
| 6,299,925 B1 | 10/2001 | Weihong et al. | |
| 6,555,675 B2 | 4/2003 | Rideout et al. | |
| 6,656,920 B2 | 12/2003 | Philip et al. | |
| 6,746,697 B2 | 6/2004 | Wolfson | |
| 7,288,270 B1 | 10/2007 | Sekharam et al. | |
| 7,501,452 B2 | 3/2009 | Troha et al. | |
| 2002/0054859 A1 | 5/2002 | Hernandez | |
| 2003/0171438 A1 | 9/2003 | Ueno | |
| 2004/0076695 A1 | 4/2004 | Gilbard | |
| 2005/0043258 A1 | 2/2005 | Bennett et al. | |
| 2005/0085485 A1 | 4/2005 | Wuthrich | |
| 2005/0090556 A1 | 4/2005 | Ueno | |
| 2006/0024248 A1 | 2/2006 | Spengler et al. | |
| 2006/0078620 A1 | 4/2006 | Desjonqueres | |
| 2006/0088643 A1 | 4/2006 | Fagal et al. | |
| 2006/0115488 A1 | 6/2006 | Morrison | |
| 2006/0177384 A1 | 8/2006 | Brown | |
| 2006/0204551 A1 | 9/2006 | Manley et al. | |
| 2007/0112026 A1 | 5/2007 | Nagamoto et al. | |
| 2007/0128284 A1 | 6/2007 | Troha et al. | |
| 2007/0264365 A1 | 11/2007 | Amebrant et al. | |
| 2008/0024385 A1 | 1/2008 | Zimmerman | |
| 2009/0062379 A1 | 3/2009 | Hsu et al. | |
| 2009/0263467 A1 | 10/2009 | Joshi | |

FOREIGN PATENT DOCUMENTS

| | | |
|---|---|---|
| CA | 2641263 | 8/2007 |
| WO | 1989009594 A1 | 10/1989 |
| WO | 2006135785 A2 | 12/2006 |
| WO | 2007092811 A2 | 8/2007 |

OTHER PUBLICATIONS

Mol Pharmacol. Apr. 1989; 35(4):469-76.

Luthin G R and Wolfe B B. J Pharmacol Exp Ther. 228(3): 648, 1984.

Ann Rheum Dis. Apr. 1992; 51(4):499-502.

Journal of the Science of Food and Agriculture, 2003, vol. 83 Issue 6, pp. 564-573.

Tsuda, A et al., "A dose-Resp;onse Study of Anticholinesterase Drugs on Contractile and Phosphatidylinositol Response of Rat Trachea", International Society for Anaesthetic Pharmacology, Anesthetic Pharmacology, 2001, vol. 92, pp. 100-105.

"Simple treatment relieves palliative care patients", Department of Human Services, Victoria Australia, Apr. 2006, http://www.dhs.vic.gov.au/humanservicenews/apr06/grape.htm.

Andersson, G. et al., Comparison of the effect of the linseed extract salinum and a methyl-cellulose preparation on the symptoms of dry mouth:, Gerodontology, Jul. 1995, vol. 12, No. 1, pp. 12-17.

Proctor, G.B. "Muscarinic receptors and salivary secretion", Journal of Applied Physiology, vol. 100, pp. 1103-1104, 2006.

Kitada, K et al., "Enhancement of oral moisture using tablets containing extract of Capparis masaikai Levi", Journal of Ethnopharmacology, Mar. 18, 2009, vol. 122, No. 2, pp. 363-366.

Orajel Dry Mouth Moisturizing Spray, Del Laboratories, Inc. http://www.dentalcompare.com/details/7071/Orajel-Dry-Mouth-Moisturing-Spray.htm.

Tao, D. et al., "The effect of chewing gum containing tea polyphanol on salivary flow rate and pH", Shanghai Kou Qiang Yi Xue, Aug. 2006, vol. 14, pp. 360-362.

TKDL KS01-110 Anuboga Vailhya Navaneetham, Part-8, Ed Mohammad Abduliah Shahib, Publisher: Thamarai Nooiagam, Chennai (Edn. 2nd, 2002).

TKDL ME02-167 Pulippan Varthyam-500. Ed. S.P. Ramachanchiran, Publisher: Thamarai Nooiagam, Chennai.

TKDL NA 4-248A Qaraabaadeen Najm-al-Ghani (20th century AD), Munshi Nawai Kishore, Lucknow, (Second Edition) 1928 AD.

TKDL AA27-5G1 Al-Abnia-'an-Haqaayiq-al-Advia (11th century AD), Tehran, Iran, 1992 AD.

TKDL RG13-29C Nigha"uratnckara"—edited and Marathi Translation by GRS Datar, BAS Tamankar, KS Mahabai, W Patel, Part-2, Vishnu Vasudev Godbole, Bombay, Edn 1867.

TKDL RS15-476 Madanapcianigha"au"—Translated by Rama Prasad, Khemaraj Shri Krishriadas Prakashan, Bombay, Edn 1998.

TKDL RS6-112 Madanapoianigha"au"—Translated by Rama Prasad, Khamaraj Shri Kishnadas Prakashan, Bombay, Edn. 1998.

Ghayur MN et al Ginger facilitates cholinergic activity possibly due to blockade of muscarinic autoreceptors in rat stomach fundus: PAK J Pharm Sci Jul. 2007, 20(3) 231-5 & Pubmed Abstract 17545109.

Vidal S. et al., "The Mouth-feel properties of grape and apple proanthocyanidins in a wine-like medium." J. Sci Food Agric 83:564-573 (online: 2003).

Speight et al., "Measurement of whole unstimulated salivary flow in the diagnosis of Sjogren's syndrom." Ann of the Rheumatic Diseases 51:499-502 (1992).

* cited by examiner

COMPOSITIONS AND METHODS FOR ALLEVIATING HYPOSALIVATION AND FOR PROVIDING ORAL COMFORT

CROSS REFERENCE

This application is a continuation-in-part application of U.S. application Ser. No. 14/551,507, filed Nov. 24, 2014, which is a continuation-in-part application of Ser. No. 13/129,210, filed May 13, 2011, which is the National Stage of International Application No., PCT/US2009/064453, filed November 2009, which claims the benefit of Provisional Application No. 61/114,359, filed Nov. 13, 2008.

FIELD OF THE INVENTION

The field of the invention is compositions and methods to alleviate or treat symptoms associated with hyposalivation and/or to provide oral comfort.

BACKGROUND

Hyposalivation and xerostomia (commonly referred to as 'dry mouth') are relatively common among a variety of people, and are especially common among the elderly, patients taking various medications (e.g., chemotherapeutic agents, antihistamines, antidepressants, diuretics, medical marijuana, cannabinoids, etc.), and individuals with high coffee or alcohol consumption. Xerostomia is also often found in patients with endocrine disorders, nutritional deficiencies, nerve damage to the face, neck, and head, and even stress. Most typically, patients suffering from hyposalivation and/or diagnosed with xerostomia, including those with Sjogren's Syndrome will have a noticeable and significant reduced flow and volume of saliva, commonly also associated with chemical changes in the saliva, all of which often presents itself in a variety of symptoms, including bad breath, thick and string-like saliva, an altered sense of taste and, in some cases, difficulty speaking or swallowing. In more severe cases, xerostomia is also associates with oral infections, sores or cracked tissue along the corners of the mouth.

Non-Sjogren's or rheumatoid/inflammatory disease sufferers are more likely to have intermittent discomfort associated with a noticeable paucity of saliva. Eighty percent of all instances of hyposalivation are directly attributable to the use of prescription drugs or over the counter medications known to interact with the central nervous system. However, even otherwise healthy individuals experience periods of hyposalivation, typically associated with high stress, physical exhaustion, speaking nervousness, or diurnal effects of hormones. For example, many individuals experience periods of hyposalivation while sleeping as mastication and general stimulation to the salivary glands is reduced during this time. While most individuals can ignore transient hyposalivation or mask it's effects by increasing water consumption, it is preferable to avoid it, if possible. Overall oral comfort is associated with sufficient saliva to create a feeling of moisture, lubrication, hydration of the soft tissues, and the ability to move the tongue and speak, swallow, and chew without discomfort. The average resting flow rates for a healthy adult are generally recognized to be about 1.5 ml per minute. When an individual's salivary output drops to about 50% of their normal resting flow, they are more likely to notice hyposalivation and its effects on their oral comfort.

There are many compositions and methods known for the treatment of xerostomia. For example, U.S. Pat. No. 4,980,177 teaches mechanical stimulation with a chewing gum that further includes hydrophilic compounds. Similarly, U.S. Pat. No. 4,997,654 teaches a chewing gum formulation with relatively high xylitol content to promote salivation and U.S. Pat. No. 6,656,920 teaches use of disaccharides in a composition to treat xerostomia. Alternatively as described in U.S. Pat. No. 4,820,506, an organic acidulant and sweetener are used to promote saliva production and/or flow. Similarly, WO 89/09594 teaches use of an organic acid in a controlled release chewing gum formulation, and U.S. Pat. App. No. 2006/0204551 teaches a synergistic combination of a food acid and a tingling sensate to promote salivation. While such compositions tend to provide at least some relief to a patient, several disadvantages nevertheless remain. For example, use of chewing gum is typically not recommended overnight and thus often limited to daytime use. Moreover, and especially where acids are employed, prolonged exposure may result in at least partial dental demineralization.

To avoid at least some of these problems, nutritionally acceptable and chemically defined compounds may be administered as described in U.S. Pat. App. No. 2007/0128284 where a sulfur-containing antioxidant such as N-acetylcysteine is combined with a polymeric base, or in U.S. Pat. App. No. 2004/0076695 where omega-3 fatty acids are used, in various compositions. In yet further known compositions, peroxidized lipids (typically plant oils) and silica are used to alleviate xerostomia as taught in U.S. Pat. App. No. 2006/0078620. In yet other known methods, glycerol may be employed to improve dry mouth conditions as noted in U.S. Pat. App. No. 2009/0263467A1. Still further known compositions include those in which certain plant extracts are used to formulate a composition for treatment of xerostomia as described in U.S. Pat. No. 4,938,963 (Yerba Santa extract) and U.S. Pat. No. 6,746,697 (*Heliopsis Longipes* extract). Yet further known compositions and methods are described in WO 2007/092811.

While at least some of these compositions can potentially provide temporary relief in a patient, several disadvantages nevertheless remain. For example, the chemical stability of some of the compounds (and even some of the plant extracts) may be problematic. Moreover, and depending on the particular formulation, the obtained effect is relatively weak and thus requires repeated administration and/or high concentration of the active ingredient, which may be prohibitive due to bad taste or solubility.

Medical marijuana has been used to treat a vast array of medical conditions. Recently legalization for recreational use has been the subject of debate. Regardless of the use there are a number of different side effects associated with administering marijuana. One of these is dry mouth or cottonmouth. Once believed to be caused by the hot smoke inhaled when smoking *cannabis*, it is now believed to be more directly related to the consumption of *cannabis*. In fact, the submandibular glands where saliva and amylase are produced contain the CB1 and CB2 cannabinoid receptors. Activation of these cannabinoid receptors occurs whenever every time *cannabis* is consumed, thus producing dry mouth. In certain compositions of medical marijuana, the active agent THC is removed, yet other cannabinoids are still present, hence the potential for hyposalivary effects of use when ingested, smoked, or otherwise used in the human body. Activation of the M3 receptors for the salivary glands allows for release of saliva when cannaboid mediated suppression is present.

Hard and Soft tissue impacts of hyposalivation are understood, including the severe levels of hyposalivation seen with chronic medically indicated *Cannabis* consumption, and include: loss of cellular and epithelial protection of a mucin containing coating over such soft tissues of the mouth, oral mucositis or inflammation of the soft tissues, fissuring or cracking of the dorsal and lateral surfaces of the tongue, glossitis, burning mouth syndrome, demineralization of teeth and caries especially of the coronal aspect, and sensitivity resulting from the loss of the protective cementum, dentin, or enamel of the surface of a tooth, and increased propensity of tooth loss, attachment loss, gingivitis, and halitosis.

A recent article in Journal of the American Dental Association, (Dental treatment planning considerations for patients using *cannabis*, Sarah Essek Grafton, DMD, Po Ning Huang, DMD Candidate, BS, Alexandre R. Vieira, DDS, MS, PhD, JADA May 2016 Volume 147, Issue 5, Pages 354-361) reported cases of gingivitis linked directly to chronic use of *Cannabis*. The study shared that gingivitis was associated with use of *Cannabis* and that dentists needed to be both aware of the association and proper treatment.

The oral tissue impacts of severe hyposalivation are painful physiologically and psychologically, expensive to treat, and can lead to severe systemic impacts such as major whole body inflammation, infection, cardiovascular, metabolic, and nutritional outcomes including the potential disability and loss of life.

Pharmaceutical companies are recognizing the health benefits afforded by use of THC and other cannabinoids for a variety of conditions including chronic pain relief, MS, arthritis, AIDS, Alzheimer's, asthma, cancer, epilepsy, glaucoma. The discovery and development of more traditional pharmaceutically standardized and modified forms of cannabinoid compounds, holds great promise but not without side effects including hyposalivation caused by activation of the CB1 and CB2 receptors found in the major salivary glands of the mouth. At this point the pharmaceutical development of cannabinoids has not found a method or way to modify the actives to avoid this serious outcome of use of otherwise beneficial drugs. It is widely accepted that cannabinoids including *cannabis* are causative of temporary hypo salivation and that relief of this condition is a desired state.

Therefore, while numerous compositions and methods to reduce symptoms of xerostomia and/or hyposalivation are known in the art, there is still a need to provide improved compositions and methods for alleviation of symptoms associated with xerostomia and/or hyposalivation, and promote overall oral comfort/feel in the general population especially those using cannabinoids in any fashion.

SUMMARY

According to the present invention compositions and methods are provided to reduce or even eliminate one or more of the symptoms associated with hyposalivation and/or xerostomia (which may be drug-induced such as use of cannabinoids, due to Sjogren's Syndrome, age, or other condition) wherein especially preferred compositions and methods will employ one, and most preferably at least two plant components. One of is most preferably isolated from a fruit and/or seed (e.g., grape, cranberry, blue berry, black berry, etc.) and the other isolated from a citrus fruit (e.g., lemon, orange, lime, grapefruit, tangerine, mandarin orange, ugli fruit, etc.). In further especially preferred aspects, the two are a synergistic combination (e.g., grape seed extract and freeze-dried lemon pulp).

Freeze-dried lemon pulp powder is obtained by first removing the peel of the lemon with it's terpenes and natural oil components which are astringent in quality and suppress salivary flow. The remaining fruit is squeezed for the removal of the juice of the lemon and its component organic acids, citric and malic, etc. These organic acids introduced into the mouth result in a bolus effect and the total release of saliva for potential immediate relief, but suppress the salivary gland ability to produce saliva for an extended period as a consequence of a pH mediated reaction. Hence if one were to introduce whole lemon powder, lemon extract of oils, flavors, lemon peel extract, or lemon juice or lemon juice powder; the effect would not be the same quality or duration as lemon pulp powder alone.

Viewed from another perspective, it is contemplated that the compositions according to the inventive subject matter will comprise a (preferably naturally occurring) proanthocyanidin and citrus fruit pulp at a concentration effective to reduce at least one symptom associated with hyposalivation and/or xerostomia.

Therefore, in one aspect of the inventive subject matter, a method of providing relief from one or more symptoms (e.g., dry mouth, bad breath, thickened saliva, altered sense of taste, difficulty speaking or swallowing) that are associated with hyposalivation in which in one step a topical composition for oral administration is formulated, wherein the composition includes a proanthocyanidin and/or a grape seed extract and citrus fruit pulp at a concentration effective to provide relief from the symptom. In another step, a test result is obtained that indicates that the proanthocyanidin and/or the grape seed extract and citrus fruit pulp provide relief from the symptom, and in yet another step, the composition is provided to a consumer in association with the test result.

In most preferred aspects, the topical formulation is a mouth rinse, a toothpaste, a dissolving strip, or a lozenge, and/or the proanthocyanidin is incorporated into the topical formulation as part of a plant extract (typically as part of a bilberry extract, cranberry extract, black currant extract, black tea extract, and/or chokeberry extract) and combined with the citrus fruit pulp. While numerous concentrations for the proanthocyanidin and/or a grape seed extract and citrus fruit pulp are contemplated, particularly suitable concentrations are relatively low and will typically be at or below 1 wt % of the topical composition.

It is generally preferred that the topical composition containing Grape seed extract comprises freeze-dried pulp powder from a citrus fruit (e.g., freeze-dried lemon pulp powder), which is most preferably present in a synergistic amount. It is postulated that one mechanism is an activation of M3 receptor activity from proanthocyanidin and/or the grape seed extract along with the citrus fruit pulp which increases salivary flow in a human.

Viewed from a different perspective, the inventor therefore also contemplate an oral care product to provide oral comfort to a person affected by a symptom of hyposalivation (e.g., dry mouth, bad breath, thickened saliva, altered sense of taste, and difficulty speaking or swallowing). Most preferably, the product comprises a composition that includes as sialagogue active ingredient a proanthocyanidin, a grape seed extract, and/or a plant extract along with the citrus fruit pulp powder that are demonstrated to have M3 receptor synergistic agonist activity at a concentration effective to alleviate a symptom associated with hyposalivation. Preferably, the composition is formulated for oral topical administration.

As noted above, it is generally preferred that the oral care product is formulated as a mouth rinse, a toothpaste, a dissolving strip, gel, gel in a tray, spray, non-dissolving strip, patch, bandage, or a lozenge, and/or that the proanthocyanidin is incorporated into the composition as part of an extract selected from the group consisting of a bilberry extract, a cranberry extract, a black currant extract, a black tea extract, and a chokeberry extract. Regardless of the source, it is further preferred that the proanthocyanidin and/or the grape seed extract are present at a concentration of equal or less than 1 wt % of the topical composition. The composition preferably includes freeze-dried pulp powder from a citrus fruit.

The present invention further provides a topical composition comprising a composition that includes as sialagogue active ingredient a proanthocyanidin, a grape seed extract, and a lemon freeze dried pulp powder in a 9 to 1 ratio with the grape seed extract that, together, elicits M3 receptor agonist activity at a concentration effective to alleviate a symptom associated with hyposalivation. The lemon pulp is a freeze dried product after the peal, pith, and juice is removed. When used in combination as described herein, a noticeable and lasting increase in salivary flow results.

Various objects, features, aspects and advantages of the present invention will become more apparent from the following detailed description of preferred embodiments of the invention.

DETAILED DESCRIPTION

The inventor has discovered that oral comfort can be provided to an individual, and particularly to an individual suffering from one or more symptoms associated with Sjogren's syndrome, xerostomia, or hyposalivation by administering a composition that comprises a grape seed extract, a proanthocyanidin, and/or a plant extract that includes a component that activates the M3 receptor in the salivary glands. In preferred aspects of the inventive subject matter, the proanthocyanidin is provided as part of a plant extract, and a freeze-dried pulp powder from a citrus fruit is added to the composition. Most typically, the composition is formulated for oral topical administration to a mucosal membrane of a lasting quality.

It should be noted that the term "hyposalivation" as used herein generically refers to a reduction in saliva production, flow, and/or volume as compared to normal saliva production, flow and/or volume generally found in a healthy, unaffected person. The term "xerostomia" as used herein refers to one specific manifestation of hyposalivation, which may be due to various causes. For example, xerostomia may be due to medication, radiation treatment, or an autoimmune disease (e.g., Sjogren's syndrome). It should also be appreciated that while contemplated compositions and methods are particularly advantageous for treatment of hyposalivation, otherwise healthy people can also experience occasional dry mouth during waking hours as well as during the night due to decreased salivary flow. The use of contemplated methods and compositions before going to bed will help such population sleep better and wake up with fresher mouth feel and breath, and will also provide increased oral comfort.

In an especially preferred aspect, a composition for relief from a symptom associated with hyposalivation includes a combination of a grape seed extract and a lemon pulp. It should be noted that the term "grape seed extract" as used herein expressly excludes grape seed oil. Viewed from a different perspective, grape seed extract as used herein represents the fraction of grape seeds that is extracted using polar and/or hydrophilic (water miscible without phase separation) solvents. In contrast, grape seed oil is the substantially water-immiscible lipid phase of grape seeds, typically comprised of linoleic acid, oleic acid, palmitic and stearic acid. Thus, grape seed oil and grape seed extract are mutually exclusive.

For example, in one especially preferred aspect of the inventive subject matter, a topical composition was prepared that included commercially available grape seed extract (N31) and freeze-dried lemon pulp powder (N600) (both obtained from VDF Futureceuticals, 819 N. Dixie Hwy., Momence, Ill. 60954) in proportions as indicated in Table 1 below with numbers indicating wt % fraction of the formulation. The freeze-dried lemon pulp powder was washed 2 times through a filter paper with 500 ml of deionized and distilled water, and then dried before mixing with grape seed extract to ensure elimination of ascorbic acid.

TABLE 1

|  | N31 (GSE) | N600 (Lemon pulp) |
| --- | --- | --- |
| Formula 50 | 0.5 | 4.5 |
| Formula 10 | 0.1 | 0.9 |
| Formula 05 | 0.05 | 0.45 |
| Formula 01 | 0.01 | 0.09 |

Using the formulation labeled "Formula 10", six subjects known to suffer from drug induced dry mouth were treated as follows: 1 mg of powder was spread on a single layer of woven cotton gauze and placed against the parotid glands on each inside side of the cheek for 5 minute exposures. Thus, total exposure was 2 mg of the topical formulation, comprising a total of 2 microgram (mcg) of grape seed extract. The results were quantitated using resting saliva collection, and humidity of tissues (cheek pouch) taken before and after the exposure as indicators. Post hoc analysis also included measurement of pH and buffering capacity of pre- and post-resting saliva samples.

Remarkably, and despite the apparent small quantity of the extracts/proanthocyanidin, apparent uniform improvement was achieved in saliva flow, saliva volume, and saliva weight (each typically having an increase of at least 10%, more typically at least 25%, even more typically at least 50%, and most typically at least 75%), which was accompanied with an increased pH indicating fresh saliva production. It should be noted that increased pH is especially advantageous as such increase reduces the likelihood of dental demineralization. Subject reactions to trial were immediate and appreciated as improved oral conditions were noted and voiced by all.

Figure 1:
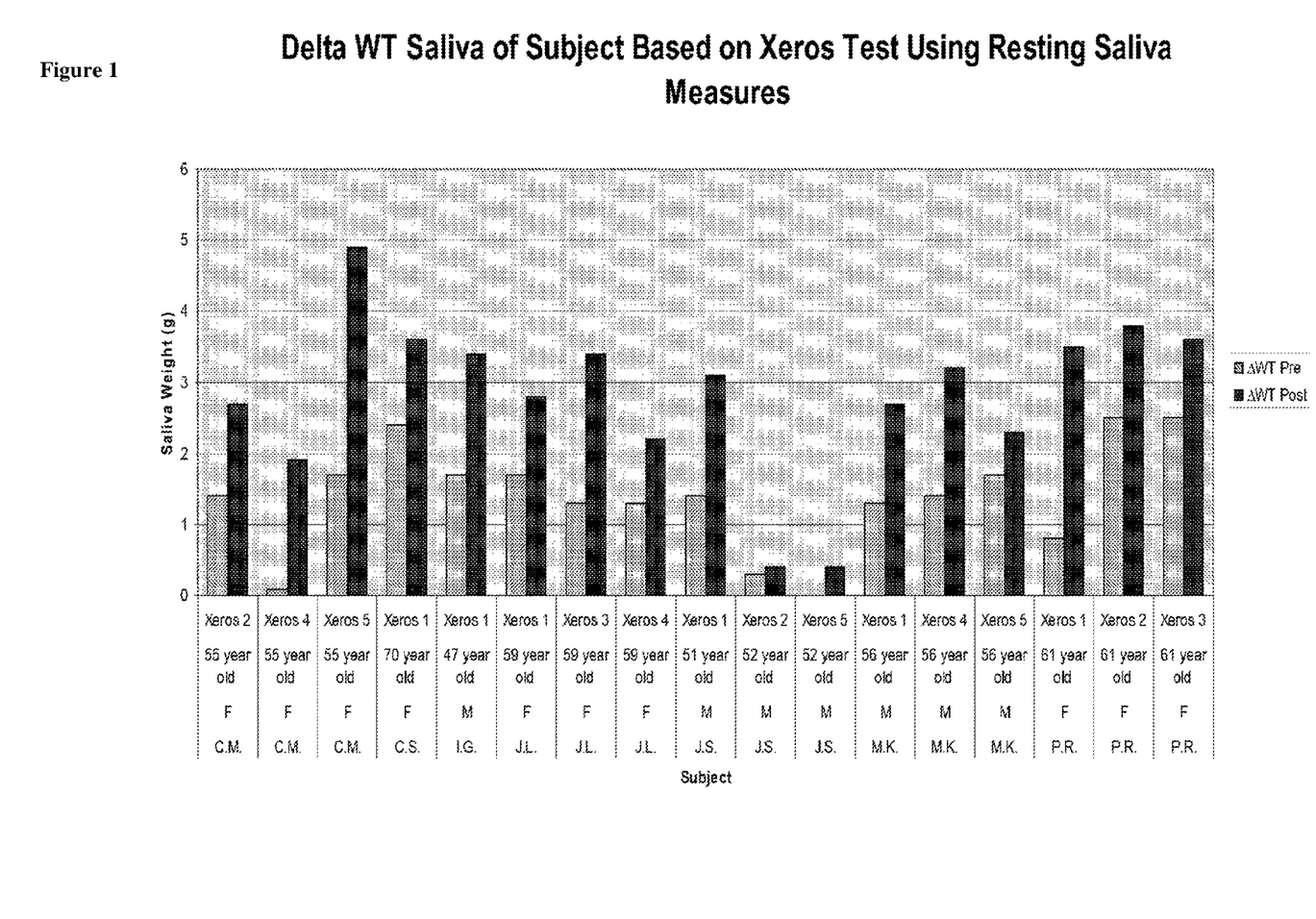
FIG. 1 is a graph depicting saliva production (by weight) in vivo before and after topical application of selected extracts according to the inventive subject matter.
Figure 2:
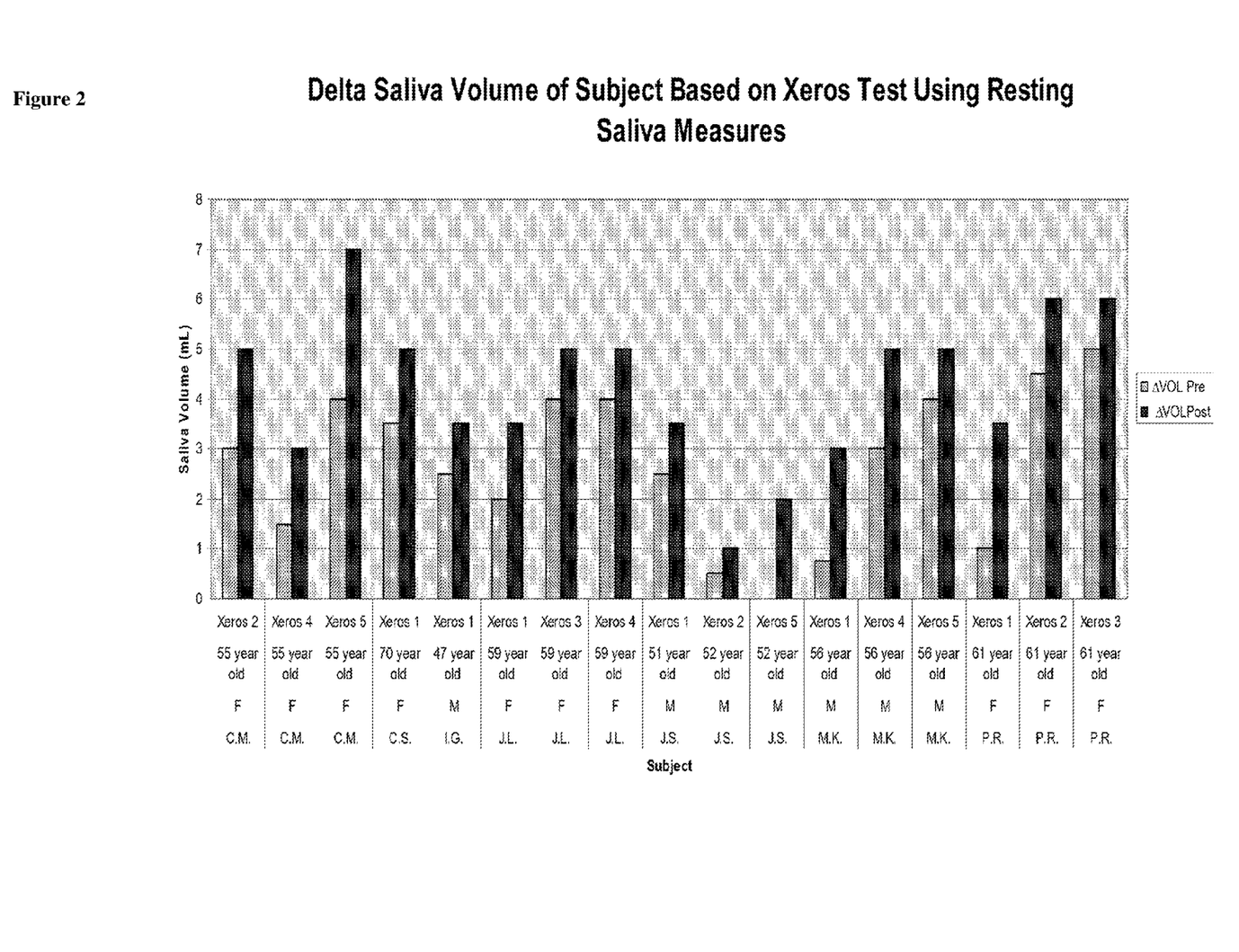
FIG. 2 is a graph depicting saliva production (by volume) in vivo before and after topical application of selected extracts according to the inventive subject matter.
Figure 3:
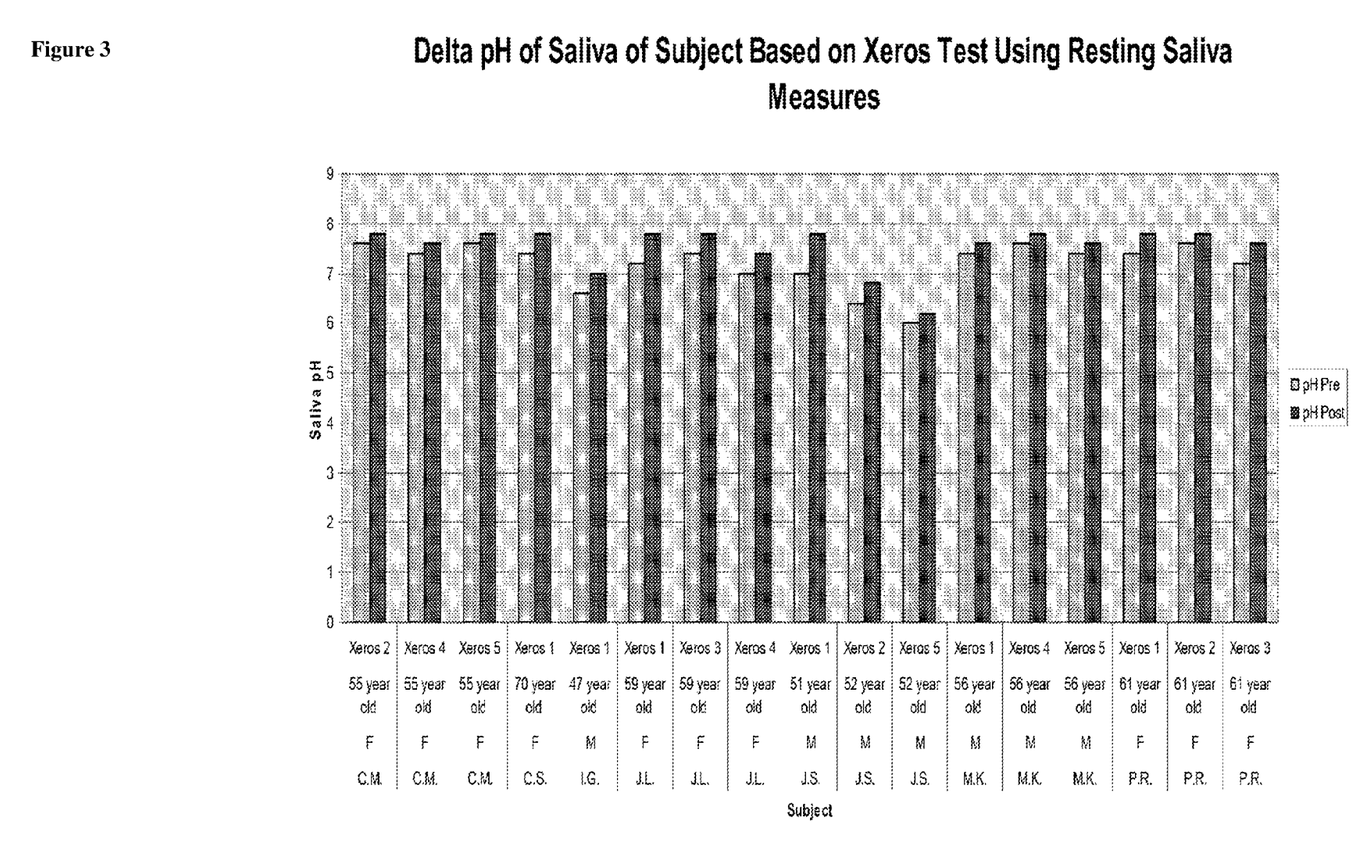
FIG. 3 is a graph depicting saliva pH in vivo before and after topical application of selected extracts according to the inventive subject matter.

Further experiments were conducted with additional compositions and combinations (only selected data provided here), and the results depicting increased weight of saliva are depicted in FIG. 1, while the results depicting increased volume of saliva are depicted in FIG. 2. The difference in pH of the saliva before and after treatment is shown in FIG. 3. More specifically, and with further reference to the FIGS. 1-3, five experimental conditions were tested and labeled as Xeros 1-5: Xeros 1 included a pre-rinse with 30 mL water for 60 sec., followed by application of DMRF10-powder on a 2 cm.times.2 cm 1 ply non-woven sponge. Xeros 2 included a pre-rinse with 30 mL water for 60 sec., followed by application of Formula 50 (F-50) on a 2 cm.times.2 cm 1 ply non-woven sponge with powder; Xeros 3 included a pre-rinse with 30 mL water for 60 sec., followed by application of 100 mg Formula 10 (F-10) in 30 mL of water for 60 sec; Xeros 4 included a pre-rinse with 30 mL water for 60 sec., followed by application of 200 mg Formula 50 (F-50) in 30 mL water for 60 sec; Xeros 5 included a pre-rinse with 30 mL water for 60 sec. (5 min collection time), followed by rinsing with Formula 50 (F-50) in 30 mL for 60 sec (5 min collection time). All probands reported that the compositions tasted good, worked fast, and provided long-lasting relief. Indeed, all probands expressed interest to continue treatment at home as the treatment significantly exceeded expectations. Continued use appeared to provide general improvement over time. Results obtained by double blind applications of the combined Grape Seed Extract and Lemon Pulp Powder formulations, demonstrate clinically and statistically relevant lasting effects in subjects of at least 6 hours duration from a single dose exposure.

Among other beneficial effects, individuals affected with hyposalivation reported reduction and in some cases even total resolution of dry mouth, bad breath, thickened saliva, altered sense of taste, and/or difficulty speaking or swallowing. Moreover, and especially where contemplated formulations are administered over a longer period, it should be noted that due to the strong antioxidant character of proanthocyanidins (especially polyphenolic proanthocyanidins), various additional benefits may be obtained, including reduction in plaque, gingivitis, and periodontal disease as well as reduction in bad breath, and mineralized tissue impacts via increased salivary flows to achieve normal states.

Moreover, several experiments associated with M3 stimulation (data not shown) demonstrated that grape seed extract and freeze-dried lemon pulp powder resulted in a synergistic stimulation of the M3 receptor. For example, where the grape seed extract and freeze-dried lemon pulp were used at a wt ratio of 9:1, activation levels of 24% were achieved, while the combined expected level of the extracts alone would have been 18% (12+6%). Remarkably, when the freeze-dried lemon pulp powder was combined with a green tea extract in the same ratio, the effect was merely additive (18%). Thus, particularly preferred combinations are those in which grape seed extract is combined with freeze-dried lemon pulp powder, and where the weight ratio of the extracts is between 25:1 and 2:1, more preferably between 15:1 and 4:1, and most preferably between 12:1 and 5:1.

Thus, it is contemplated that a method of providing relief from a symptom associated with hyposalivation includes a step of formulating a (most preferably topical) composition for oral administration that includes at least one of a proanthocyanidin and a grape seed extract at a concentration effective to provide relief from the symptom. It is generally preferred to obtain a test result that indicates that the proanthocyanidin and/or grape seed extract provides relief from the symptom. In especially preferred methods, the composition is made available to a user or wholesale entity or retailer for a variety of oral care applications.

For example, another embodiment of the present invention is its application in the prevention of dry mouth or cottonmouth in individuals consuming cannabinoids including marijuana or *cannabis* in any form. When administered immediately prior, during or after consumption of *cannabis*, the present invention provides relief from symptoms of cannabinoid or *cannabis*-induced hyposalivation.

Another embodiment of the present invention is the combination of Grape Seed Extract and Lemon Pulp Powder as a surrogate reagent with any diagnostic assessment of saliva from general and affected populations involving metabolic conditions like diabetes. Metabolic conditions like diabetes adversely affect the total flow volumes and component characteristics of saliva as compared with normal unaffected populations. It is important to have a suitable volume of fresh saliva expressed to perform assays. The generally observed depressed volumes while important indicators and signs of metabolic diseases, are as depressed absolute volumes not correlated by amounts to the metabolic state of the patient as compared to normal populations. However biomarkers like salivary containing: C-Reactive protein, Insulin, iL-6 and more, are being recognized as important to the identification and treatment measurement of metabolic disorders. Their presence in saliva has more to due with detection and minor changes in structure than total percentage of sample, thereby making baseline volumes of whole saliva of critical importance to the assay. Most protocols today call for whole unstimulated collection after a 1 hour fasting which by itself again depresses the production potential for saliva in affected and unaffected individuals, seen more in affected individuals. The unique characteristics for lasting saliva flow in the combination product having Grape Seed Extract and Lemon Pulp Powder when applied before the 1 hour fasting period to provide a more available and normalized volume of saliva for collection thereby decreasing the chances for inadequate volumes of unstimulated saliva. This preemptive application and resultant increase of saliva flow due to the combination of Grape Seed Extract and Lemon by the individual is not the same as if immediately collected stimulation. The salivary glands when exposed to immediate stimulation and different forms of releasing saliva, like chewing of wax, or application of citric acid, release what components are presently found in the salivary gland acini, which in a depressed state, are older and perhaps degraded, BUT as the M3 stimulation due to application of the combination of Grape Seed Extract and Lemon Pulp Powder exhibits, the salivary flow increases and remains elevated for up to 6 hours duration after a single application of the combination indicting fresh saliva and components therein. This would provide adequate volumes of saliva available for detection assays without breaking the existing reasons for the 1 hour fasting period.

While not wishing to be bound by any specific theory or hypothesis, the inventors contemplate that the fruit/seed extract/proanthocyanidins as well as freeze-dried lemon or other citrus pulp powder/s act as M3 receptor (Type 3 muscarinic acetylcholine receptor) agonists, most likely in a synergistic manner. Therefore, it should also be recognized that all plant extracts that activate the M3 receptor are deemed suitable for use herein as standalone compound, synergistic additive, and/or adjuvant.

Viewed from a different perspective, an oral care product is contemplated that will provide oral comfort to a person affected by one or more symptoms of hyposalivation. Especially contemplated care products include a composition that includes a grape seed extract, a proanthocyanidin, and/or a plant extract that is demonstrated to have M3 receptor agonist activity as sialagogue active ingredient at a concentration effective to alleviate at least one symptom associated with hyposalivation, wherein the composition is formulated for oral topical administration. It should be noted that the term "sialagogue active ingredient" when used in conjunction with the grape seed extract, a proanthocyanidin, and/or a plant extract that is demonstrated to have M3 receptor agonist activity means that the grape seed extract, the proanthocyanidin, and/or the plant extract are the active ingredients that promote salivary production and flow. Moreover, the term "oral topical administration" of a composition or formulation refers to contacting the oral tissues with the composition or formulation over a period that is significantly longer that the contact time typically observed for ingestion of the composition or formulation. While any ingested (swallowed) composition or formulation will at least in part contact oral tissues, oral administration of a composition or formulation for the purpose of ingesting the composition or formulation is expressly excluded from the scope of the definition provided herein. Viewed from a different perspective, oral topical administration of a composition or formulation will achieve the intended purpose (e.g., increase in salivary flow or volume) by contact with the oral tissue and without ingestion of the composition or formulation.

Regardless of the particular ingredients and formulation, it should be noted that the increase in saliva production, flow, and/or volume, and/or increase in M3 activity using contemplated compositions may be verified in numerous manners well known in the art. For example, M3 agonist activity can be measured using a commercially available test service (e.g., test #252810 from MDS Pharma Sciences, 2200 Renaissance Blvd., Suite 400, King of Prussia, Pa. 19406) or in recombinant cells or cells obtained from a mammal substantially following a test protocol as described in Mol Pharmacol. 1989 April; 35(4):469-76 and in Luthin G R and Wolfe B B. J Pharmacol Exp Ther. 228(3): 648, 1984. A typical example of such activation using contemplated compounds and compositions is presented in FIG. 4. Here, it should be particularly appreciated that M3 agonist activity was observed at remarkably low concentrations of contemplated compounds and compositions. For example, FC-03 (Green tea extract commercially available from VDF FutureCeuticals with at least 95% polyphenol content), FC-06 (Vitaberry plus extract commercially available from VDF FutureCeuticals with wild blueberry powder, grape seed extract powder, raspberry seed extract powder, cranberry powder, prune powder, tart cherry powder, wild bilberry powder, and silica dioxide), and FC-09 (Vitagrape extract commercially available from VDF FutureCeuticals with at least 90% total phenolic content) provided an at least 10% activation in the Sf9 assay over control at concentrations of less than 50 ppm, more typically less than 30 ppm, and most typically less than 20 ppm. Thirteen additional extracts comprising proanthocyanidins were tested and showed similar activity at the concentrations tested (data not shown). Therefore, it should be appreciated that in at least some aspects of the inventive subject matter, various oral care formulations may be provided in which the grape seed extract, proanthocyanidin, and/or plant extract (that is demonstrated to have M3 receptor agonist activity) has a concentration effective to achieve upon oral topical administration a concentration that is equal to or below 100 ppm, more typically equal to or below 50 ppm, and most typically equal to or below 25 ppm in the fluid that contacts the oral tissue (and particularly oral mucosal tissue).

Alternatively, simple in vivo tests measuring saliva flow can be performed following well-known methods (e.g., Ann Rheum Dis. 1992 April; 51(4):499-502). Thus, test results will be available from human (or other mammalian) subjects as well as from cell cultures. Thus, a test result may be obtained (by the provider of the composition or other party, including contract test laboratory) directly by in vivo tests on human subjects or by performing the M3 agonist activity test, or indirectly by having the test(s) performed in a contract or otherwise affiliated laboratory, and even by having an independent and unaffiliated third party perform the test(s) and publish the test result. Especially contemplated test results will include those in which increase in saliva flow and/or M3 activation is reported as a function administration of the composition to a mammal (or other animal) or cells. Such report preferably provides qualitative information on the amount and/or type of the composition used and/or the increase in saliva flow and/or M3 activation achieved. Alternatively, or additionally, qualitative test results may also be provided that indicate in a generic manner that the composition is effective to increase salivary flow and/or volume, or effective to reduce a symptom associated with hyposalivation. Most typically (but not necessarily), the composition used for the test result has the same or similar ingredients than the composition that is marketed or otherwise provided to a consumer.

Thus, in especially preferred aspects of the inventive subject matter, the compositions contemplated herein will be provided to a consumer (typically the user) in association with the test result to inform or suggest to the consumer that the composition is effective to increase flow and/or volume of saliva and/or M3 activity. The term "in association with" is therefore meant to include any activity that logically (and most preferably also physically) couples the composition with the test result. For example, logical coupling includes displaying, printing, or otherwise providing information of the test result while making reference to the composition (e.g., displaying the test result and the composition). More preferably, however, the test result is physically associated with the composition. For example, such physical association may be performed by printing the test result on the container or packaging that holds the composition.

Of course, it should be appreciated that the above described exemplary formulations are merely illustrative with regard to the specific composition, and that numerous alternative compositions are also deemed suitable for use herein. For example, the proanthocyanidin may be provided as a relatively pure and isolated composition (e.g., purity greater than 50 mol %, more typically greater than 70 mol %, and most typically greater than 90 mol %), which may include a relatively complex mixture of chemically diverse polyphenols, or which may be produced by controlled oligomerization and/or polymerization of one or more species of polyphenolic compounds. Thus, contemplated proanthocyanidin compositions may be synthetic, or more preferably, isolated (e.g., as aqueous or alcoholic extracts) from one or more plant materials (typically fruit, seed, bark, or leaves), and especially from bilberry, cranberry, black currant, black tea leaves, and chokeberry. Consequently, it should be noted that the fruit/seed extract may be a multi-component extract that is more or less enriched in one or more components. Therefore, suitable extracts may include extracts prepared with one or more solvents, which may be further processed using one or more chromatographic steps.

With respect to the grape seed extract, it is generally preferably that the grape seed extract is commercially available (e.g., VDF FutureCeuticals), but also other extracts deemed suitable so long as such extracts provide an increase in saliva flow when used as described herein. For example, suitable alternative grape seed extracts are aqueous extracts, which may also involve use of a co-solvent (e.g., alcohols, ethyl acetate, etc.). While it is generally preferred that the solvent is at least partially removed from the extract to provide a solid or powder extract, appropriate extracts may also include at least a portion of the solvent and be therefore an aqueous or alcoholic solution.

On the other hand, as proanthocyanidins are commonly found in many plants and parts thereof (e.g., apple skin, pine bark, cinnamon bark, grape seed, grape skin, cocoa seed, bilberries, cranberries, black currants, choke berry, etc.), contemplated compositions may also include those where the proanthocyanidin is part of an extract from such plants or parts of the plant. As noted before, there are numerous manners of preparing plant extracts to enrich proanthocyanidins known in the art, and all of those are deemed suitable for use herein. Furthermore, it should be appreciated that the proanthocyanidins may also be present in already prepared compositions such as red wine, buckthorn oil, etc. Thus, all known proanthocyanidin/citrus extract-containing preparations are also deemed suitable for use herein.

As used herein, the term "proanthocyanidin" refers to an oligomeric or polymeric flavonol, which is typically found in fruits, bark, leaves, and seeds of various plants. It is noted that proanthocyanidins from leaves are generally less preferred, and in some aspects even excluded (e.g., leaves of *Camellia sinensis*). Most typically, proanthocyanidins will be a collection of chemically diverse oligomeric or polymeric flavonols. Still further, it is noted that resveratrol and oligomeric forms thereof are also considered a proanthocyanidin herein. Still further, it should be recognized that all of the proanthocyanidins contemplated herein may be further covalently bound to a glycosidic moiety (which may be a hexose, pentose, or even a disaccharide).

Typically, the quantity of the proanthocyanidins and/or grape seed extract will be at least 0.1-1 microgram per dose administered, more typically at least 10 microgram, and most typically at least 50 microgram. However, higher doses are also contemplated, especially where the proanthocyanidin is in a liquid formulation or controlled release formulation. Therefore, contemplated compositions may comprise between 0.01 wt % (and in some cases even less) and 10 wt % (and even higher) one or more proanthocyanidins and/or grape seed/plant extracts, especially where the composition is in liquid form or in a paste form and more typically between 0.1 wt % and 10 wt %. On the other hand, and especially where the composition is a solid composition (e.g., powder, dissolvable strip, lozenge), contemplated compositions may comprise between 1 wt % (and in some cases even less) and 75 wt % (and even higher) one or more proanthocyanidins and/or grape seed/plant extracts.

However, it should be noted that in preferred aspects of the inventive subject matter the proanthocyanidin (grape seed extract or plant extract) is present in relatively small quantities (typically less than 1 wt % of the administered composition) to achieve the desired effect. It should be particularly appreciated that the above findings are highly unexpected as proanthocyanidins and plant extracts comprising proanthocyanidins are known to have bitter taste and to produce an astringent sensation characterized as "drying", "chalky", or "adhesive" (e.g., Journal of the Science of Food and Agriculture, 2003, Volume 83 Issue 6, Pages 564-573), which is contrary to the effect observed at the concentrations presented herein. Thus, contemplated compounds and compositions will have an effective window in which the compounds and compositions will have a beneficial effect (increase in salivary production, flow and/or pH), below which no or only unsatisfactory effect is observed, and above which the beneficial effect turns into an undesirable effect. In most compositions and uses, the therapeutic or prophylactic window is between 0.1 mcg and 100 mcg per application, more typically between 1 mcg and 50 mcg per application, and most typically between 2 mcg and 20 mcg per application. Viewed from a different perspective, the therapeutic or prophylactic window in a composition (with respect to concentration of the proanthocyanidins and plant extracts comprising proanthocyanidins) will be between 0.01 wt % and 5 wt %, more typically between 0.1 wt % and 1 wt %, and most typically between 0.2 wt % and 0.5 wt %.

Contemplated compositions will also include freeze-dried pulp powder from citrus fruit, and particularly a lemon. Especially suitable freeze-dried powders include lemon and lime pulp, wherein the freeze-dried powder may be prepared from the remaining pulp after extracting the peel and juice from the citrus fruit. Depending on the type of fruit material, such commercially available materials may be dehydrated and prepared in form of powders or freeze dried films, slurries, or left in "as found" states. Most preferably, the proanthocyanidin (or grape seed extract or M3 activating plant extract) composition and the fruit pulp powder are in a wt % ratio of between 1:100, more typically in a ratio between 1:5 to 1:50 and most typically in a ration between 1:10 to 1:30). However, other ratios are also deemed suitable and will typically depend on the particular type of formulation, desired flavor profile, etc.

Unlike a lemon extract, lemon freeze-dried powder is the pulp with the peel and their oils (i.e. terpenes) removed as well as the juice and its organic acids and vitamins. The remaining pulp is then freeze-dried to obtain the powder. The lemon pulp powder provides fiber, antioxidants, bioflavonoids, and carotenoids found in raw organically grown lemons, but without the terpenes or essential oils of the peel or the citric and malic acids from the juice. It is believed, and the basis for the invention, that the observed effect results from the synergy of the carotenoids and bioflavonoids acting in a synergistic manner with the proanthrocyanidins from the Grape Seed Extract to activate the M3 receptor for an extended period of time unlike either component alone. In fact, the presence of the terpenes and essential oils of the peel are believed to suppress M3 activity, resulting in astringent responses or no saliva release or alternatively with a transient release of saliva but not the extended benefit that is demonstrated in clinical studies from the present invention. The observed bolus saliva release in the presence of the organic acids citric, malic, etc due to the pH difference and not an activation of the M3 receptor, similar to the effect seen with vinegar which also contains similar organic acids The pH related release does not last more than a few minutes, compared to the 6 hour increase in salivary production seen in the present invention.

When the freeze-dried pulp powder is combined with the Grape Seed Extract according to the present invention, the clinical effects described herein are observed. These effects include, in part, an increased and lasting salivary flow demonstrated in various clinical studies. The effect is also dependent upon the amount of material used as to much material applied at the same time depresses the salivary function due to the innervation pathways impacted by the exposure are both capable of agonistic and antagonistic responses. Accordingly, an ideal amount of Grape Seed Extract and lemon pulp powder in the ratio and dose described in the present invention provides the minimum requirement needed for lasting relief of the symptoms of hyposalivation described herein.

Where desired, additional compounds can be added to the compositions contemplated herein, and particularly preferred compounds include those that increase palatability of the composition or formulation. Therefore, particularly preferred additional compounds include sweeteners (and especially artificial sweeteners) and flavoring agents (most preferably, essential oils or artificial flavors). The determination of particular amounts of these additional agents is well within the skill of the ordinary artisan and therefore not further elaborated on.

With respect to formulations comprising contemplated compounds and compositions, it is generally preferred that the compounds and compositions are formulated for topical oral administration, most preferably in a nutritionally or pharmaceutically acceptable carrier, most preferably in a presentation that allows a user to administer the composition in an outpatient or home setting. For example, suitable formulations include solid formulations such as free flowing powders (may be impregnated onto a carrier, including floss, Q-tip, and chewing gum), dissolvable strips, tablets, lozenges, etc., and liquids and gel formulations such as rinses, sprays, toothpaste, ointments, foams, etc. Moreover, suitable formulations may further include polymers for adhesion and sustained release, flavoring agents, thickeners, emulsifiers, humectants as known in the art of oral care products. Still further contemplated appropriate formulations are described in WO 2007/092811, which is incorporated by reference herein. Most preferably, contemplated compositions will be formulated to provide immediate effect and to sustain the effect over a period of at least 60 minutes, more typically at least 4 hours, and most typically at least 8 hours. Therefore, controlled release formulations are especially included herein. For example, and where desired, contemplated formulations may also be prepared as sustained release formulations, pharmaceutical preparation for local and/or systemic delivery, as pills, as a food additive to make dry/sticky food easier to eat/swallow, as a functional drink, and as artificial saliva extender, etc. In especially preferred alternative aspects, contemplated compositions may be combined with medication that is known to produce dry mouth. Such combination may be integrated into the formulation of the medication, or as supplement together with the formulation.

The references recited herein are incorporated herein in their entirety, particularly as they relate to teaching the level of ordinary skill in this art and for any disclosure necessary for the commoner understanding of the subject matter of the claimed inventions. It should be apparent to those of ordinary skill in the art that many more modifications besides the embodiments already described are possible without departing from the scope of the invention or the inventive concepts herein. The inventive subject matter, therefore, is not to be restricted except in the spirit of the appended claims. Accordingly, the scope of the invention is determined by the scope of the following claims and their equitable Equivalents.

I claim:

1. A composition for treating cannabinoid-induced hyposalivation in a human comprising:
    i. component "a" having a combination of a proanthocyanidin and a grape seed extract such that the combination activates Muscarinic 3 receptors in the human's mouth; and
    ii. component "b" comprising a freeze dried powder from citrus pulp devoid of ascorbic acid capable of activating Muscarinic 3 receptors in the human's mouth,
    where components "a" and "b" are combined in a ratio effective to alleviate at least one symptom associated with hyposalivation induced by the use of cannabinoids for a period of time from approximately 5 min up to approximately 6 hours after topical application to the human's mouth mucous membrane, wherein the weight ratio of the grape seed extract to component "b" is 9:1.

2. The composition of claim 1, wherein the composition increases the release of saliva for a period of time from approximately 5 min up to approximately 6 hours after topical application on human mucus membranes in the mouth.

3. The composition of claim 1, wherein components "a" and "b" are combined in a ratio effective to protect soft and hard oral tissues for a period of time from approximately 5 min up to approximately 6 hours after topical application on the human mucus membranes of the mouth.

4. A method for treating cannabinoid-induced hyposalivation in a human's mouth comprising:
    a. formulating a topical composition for application to the mouth comprising:
        i. component "a" having a combination of a proanthocyanidin and a grape seed extract such that the combination activates Muscarinic 3 receptors in the human's mouth; and
        ii. component "b" comprising a freeze dried powder from citrus pulp devoid of ascorbic acid capable of activating Muscarinic 3 receptors in the human's mouth,
    where components "i" and "ii" are combined in a ratio effective to alleviate at least one symptom associated with hyposalivation induced by the use of cannabinoids for a period of time from approximately 5 min up to approximately 6 hours after topical application, wherein the weight ratio of the grape seed extract to component "b" is 9:1,
    b. administering to mucosal membranes in the human's mouth an effective amount of the topical composition from step "a" for a period of time that alleviates at least one symptom associated with hyposalivation.

5. The method of claim 4, wherein administering to the mucosal membrane is with an oral rinse, erodible film, toothpaste, gel, lozenge, gum, confectionery, tablet, powder, spray, or any combination therein.

6. The method of claim 4, wherein administering to the mucosal membrane is immediately prior to the human consuming a cannabinoid.

7. The method of claim 4, wherein administering to the mucosal membrane is simultaneous with the human consuming a cannabinoid.

8. The method of claim 4 wherein the cannabinoid-induced hyposalivation is in humans having burning mouth syndrome, mucositis, fissured tongue, or other deleterious tissue effects resulting from suppressed salivary function.

* * * * *